(12) United States Patent
Sakaguchi

(10) Patent No.: US 8,901,348 B2
(45) Date of Patent: Dec. 2, 2014

(54) METHOD FOR MANUFACTURING POLYOXYETHYLENE ALKYL ETHER ACETIC ACID

(75) Inventor: Akira Sakaguchi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/122,528

(22) PCT Filed: Jun. 7, 2012

(86) PCT No.: PCT/JP2012/064684
§ 371 (c)(1),
(2), (4) Date: Nov. 26, 2013

(87) PCT Pub. No.: WO2012/169585
PCT Pub. Date: Dec. 13, 2012

(65) Prior Publication Data
US 2014/0088323 A1    Mar. 27, 2014

(30) Foreign Application Priority Data

Jun. 10, 2011 (JP) ................................. 2011-129697
Oct. 27, 2011 (JP) ................................. 2011-235981

(51) Int. Cl.
*C07C 51/235* (2006.01)
*C07C 51/16* (2006.01)
*B01J 23/644* (2006.01)
*C07C 59/125* (2006.01)

(52) U.S. Cl.
CPC ............... *C07C 51/16* (2013.01); *C07C 51/235* (2013.01); *B01J 23/644* (2013.01); *C07C 59/125* (2013.01)
USPC ........................................................ 562/538

(58) Field of Classification Search
CPC .............................. C07C 41/03; C07C 51/235
See application file for complete search history.

(56) References Cited

U.S. PATENT DOCUMENTS 2,914,484 A * 11/1959 Monson et al. ............... 516/183
4,233,460 A   11/1980 Willis et al.
4,976,893 A   12/1990 Leupold
5,495,045 A    2/1996 Fried
6,476,258 B1 * 11/2002 Komatsu et al. ............. 562/421

FOREIGN PATENT DOCUMENTS

| JP | 54-79229 A | 6/1979 |
| JP | 54-84523 A | 7/1979 |
| JP | 65-167248 A | 12/1980 |
| JP | 61-293948 A | 12/1986 |
| JP | 62-198641 A | 9/1987 |
| JP | 4-221339 A | 8/1992 |
| JP | 2903187 B2 | 6/1999 |
| JP | 2000-95726 A | 4/2000 |
| JP | 200095726 A * | 4/2000 |

OTHER PUBLICATIONS

White et al, Basic Energy Sciences Advisory Committee Subpanel Workshop Report, Opportunities for Catalysis in the 21st Century, 2002, pp. 1-47.*
International Search Report issued in PCT/JP2012/064684 mailed Sep. 4, 2012.
International Preliminary Report on Patentability and Written Opinion of the International Searching Authority for International Application No. PCT/JP2012/064684, dated Dec. 10, 2013.
Machine translation of Japanese Application No. 2000-95726-A, published Apr. 4, 2000.
Machine translation of Japanese Application No. 4-221339-A, published Aug. 11, 1992.
Machine translation of Japanese Application No. 54-84523-A, published Jul. 5, 1979.

* cited by examiner

*Primary Examiner* — Paul A Zucker
(74) *Attorney, Agent, or Firm* — Birch, Stewart, Kolasch & Birch, LLP

(57) ABSTRACT

The invention relates to a method for manufacturing a polyoxyethylene alkyl ether acetic acid, including feeding oxygen into a liquid phase containing polyoxyethylene ether having a hydrocarbon group at the end (hereinafter, it may also be referred to as a polyoxyethylene alkyl ether) and water, and dehydrogenating and oxidizing the polyoxyethylene alkyl ether in the presence of a platinum catalyst, in which the mass ratio between the total mass of the polyoxyethylene alkyl ether and the polyoxyethylene alkyl ether acetic acid and the mass of water in the liquid phase ((polyoxyethylene alkyl ether+polyoxyethylene alkyl ether acetic acid)/water) is 60/40 to 95/5.

18 Claims, No Drawings

METHOD FOR MANUFACTURING POLYOXYETHYLENE ALKYL ETHER ACETIC ACID

FIELD OF THE INVENTION

The present invention relates to a method for manufacturing a polyoxyethylene alkyl ether acetic acid.

BACKGROUND OF THE INVENTION

A polyoxyalkylene alkyl ether acetic acid such as a polyoxyethylene alkyl ether acetic acid is a polyoxyalkylene alkyl ether compound having an end substituted with a carboxylic acid, and it is known as a surfactant that may be used for cosmetics, an emulsifying agent, a solubilizing agent, a dispersant, a gelling agent, a cleansing base, or the like.

Properties of a polyoxyalkylene alkyl ether acetic acid can be adjusted by changing pH. As a polyoxyalkylene alkyl ether acetic acid has excellent resistance to hard water and an aqueous solution thereof is stable against various polyvalent metal ions such as calcium or aluminum and has a mild action on the skin, it is expected to be applied for various uses.

As a method for manufacturing a polyoxyalkylene alkyl ether acetic acid such as a polyoxyethylene alkyl ether acetic acid, a method of an organic chemical carboxymethylation of a terminal hydroxyl group of a polyoxyalkylene alkyl ether by reacting monochloroacetic acid to a polyoxyalkylene alkyl ether in the presence of a base such as sodium hydroxide is generally used [hereinbelow, referred to as "carboxymethylation"].

In JP-A 62-198641, a method for producing a salt of a polyoxyethylene alkyl ether acetic acid by dehydrogenating and oxidizing a polyoxyethylene alkyl ether in an aqueous solution using a noble metal catalyst in the presence of a base such as sodium hydroxide is disclosed [hereinbelow, referred to as "alkali neutralization oxidation"].

In JP-A 4-221339, a method for producing a polyoxyethylene alkyl ether acetic acid by dehydrogenating and oxidizing a polyoxyethylene alkyl ether using a noble metal catalyst in the absence of a base is disclosed [hereinbelow, referred to as "non-neutralization oxidation"].

U.S. Pat. No. 5,495,045 discloses production of an alkoxyalkyl carboxylic acid from an alkoxyalkanol in the presence of a cerium salt. JP-A 61-293948 discloses production of a carboxylic acid from a primary alcohol in the presence of a platinum catalyst. JP-B 2903187 discloses production of a polyoxyethylene alkyl ether acetic acid by oxygen-oxidization of R—O—(CH2CH2O)n-H in the presence of a catalyst containing platinum or palladium and bismuth or lead. JP-A 54-079229 discloses a method for oxidizing polyoxyethylene ether by oxygen-oxidization of R—O—(CH2CH2O)n-H in the presence of a platinum carbon catalyst.

SUMMARY OF THE INVENTION

The present invention relates to a method for manufacturing a polyoxyethylene alkyl ether acetic acid by feeding oxygen to a liquid phase containing a polyoxyethylene alkyl ether having a hydrocarbon group at the end (hereinbelow, it may be referred to as a polyoxyethylene alkyl ether) and water, and dehydrogenating and oxidizing the polyoxyethylene alkyl ether in the presence of a platinum catalyst, in which the mass ratio between the total mass of the polyoxyethylene alkyl ether and the polyoxyethylene alkyl ether acetic acid and the mass of water in the liquid phase (i.e., total mass of polyoxyethylene alkyl ether and polyoxyethylene alkyl ether acetic acid/mass of water) is 60/40 to 95/5.

DETAILED DESCRIPTION OF THE INVENTION

The carboxymethylation in a conventional art has problems below:
1) monochloroacetic acid is unstable in water, and thus undergoes decomposition during the reaction, and
2) a large amount of inorganic salts are generated as side products in the reaction product, so that the inorganic salts need to be removed by an operation such as washing or the like.

The alkali neutralization oxidation of JP-A 62-198641 also has problems, for example, including:
1) a carboxylic acid salt needs to be subjected to an acid decomposition to obtain a polyoxyethylene alkyl ether acetic acid as a free acid and a large amount of inorganic salts derived from a base are generated as side products, and
2) a step of concentrating the polyoxyethylene alkyl ether acetic acid is needed.

In the non-neutralization oxidation which does not use a base, catalytic activity is lowered in accordance with the progress of the reaction.

In particular, it was found out by the inventors of the present invention that, when a polyoxyalkylene alkyl ether acetic acid having an average added mole number of the alkyleneoxy group of 6 mole or less is manufactured from the starting material of a polyoxyalkylene alkyl ether that has been manufactured by adding an alkylene oxide to an alcohol, the reaction rate (also referred to as conversion rate) decreases (cannot be improved any further).

Accordingly, the present invention provides a method for manufacturing a polyoxyethylene alkyl ether acetic acid which does not produce inorganic salts as side products and does not decrease in the catalytic activity according to the progress of the reaction, but has a high productivity.

Provided by the invention is a method for manufacturing a polyoxyethylene alkyl ether acetic acid which does not produce inorganic salts as side products or require a complicated operation for concentration, but has high productivity.

The inventors of the present invention found that, by having the mass ratio between the total mass of the polyoxyethylene alkyl ether and the polyoxyethylene alkyl ether acetic acid and the mass of water in the liquid phase within a predetermined range, a significant increase in viscosity in accordance with the reaction can be suppressed and side production of an aldehyde compound can be suppressed so that a polyoxyethylene alkyl ether acetic acid as an intended product can be manufactured with high production efficiency, and thus completed the invention accordingly.

In the present invention, the term "liquid phase" means a liquid phase in every step including the time of starting the reaction.

In the manufacturing method of the present invention, a polyoxyethylene alkyl ether acetic acid can be obtained at a high effective concentration only by having a process of filtering the catalyst after completion of the reaction without requiring a removing operation of inorganic salts or a complicated operation for concentration.

In the manufacturing method of the present invention, a polyoxyethylene alkyl ether acetic acid can be obtained efficiently as there is no decrease in catalytic activity in accordance with the progress of the reaction.

When the polyoxyethylene alkyl ether acetic acid obtained by the present invention is used for a body cleansing agent composition, for example, an excellent effect in terms of sense of use, foam generation, and a mild skin irritation property, or the like is obtained.

The hydrocarbon group of the polyoxyethylene ether having a hydrocarbon group at the end, which is used for the manufacturing method of the present invention, may contain an alicyclic hydrocarbon group, an aromatic hydrocarbon group, or the like in addition to an aliphatic hydrocarbon group.

The polyoxyethylene alkyl ether is preferably a compound represented by the following formula (I) or (III). From the viewpoint of improving a production yield and a reactivity, a compound represented by the following formula (I) is more preferable.

$$R\text{—}(CH_2\text{—}O\text{—}CH_2)_n\text{—}CH_2OH \quad (I)$$

In formula (I) and formula (II), R represents a hydrocarbon group having 3 to 21 carbon atoms and n represents an average added mole number of an ethyleneoxy group ($CH_2$—O—$CH_2$), which is a number of 0.1 to 30.

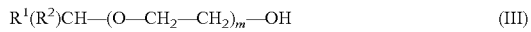

$$R^1(R^2)CH\text{—}(O\text{—}CH_2\text{—}CH_2)_m\text{—}OH \quad (III)$$

In formula (III), $R^1$ and $R^2$, each independently, represents a linear alkyl group having 1 to 20 carbon atoms, total number of carbon atoms in $R^1$ and $R^2$ is 3 to 21, and m represents an average added mole number of an ethyleneoxy group (O—$CH_2$—$CH_2$), which is a number of 1.1 to 30.

R or the like in formula (I) can be suitably determined, according to intended performance, use or the like, within the range as defined in the above.

R in formula (I) is a hydrocarbon group having 3 to 21 carbon atoms, more preferably a hydrocarbon group having 5 to 15 carbon atoms, even more preferably a hydrocarbon group having 7 to 13 carbon atoms, and even more preferably a hydrocarbon group having 9 to 13 carbon atoms.

As for the hydrocarbon group of R, a saturated or unsaturated aliphatic hydrocarbon group having a linear, branched, or cyclic structure is preferable. A linear or branched alkyl group or alkenyl group is more preferable. A linear or branched alkyl group is even more preferable, and a linear alkyl group is even more preferable.

Examples of the linear or branched alkyl group, which is represented as R in formula (I), include such as a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and a heneicosyl group.

From the viewpoint of exhibiting the performance as a surfactant, the aliphatic hydrocarbon group is even more preferably a pentyl group, a hexyl group, a heptyl group, an octyl group, a nonyl group, a decyl group, an undecyl group, a dodecyl group, a tridecyl group, a tetradecyl group, or a pentadecyl group, and even more preferably a nonyl group, a decyl group, an undecyl group, a dodecyl group, a tridecyl group, a tetradecyl group, or a pentadecyl group.

Examples of the linear or branched alkenyl group, which is represented as R in formula (I), include such as a propenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icocenyl group, and a henicocenyl group. Linear or branched alkadienyl groups or alkatrienyl groups such as various octadecadienyl groups or octadectrienyl groups can also be used.

Examples of the aliphatic hydrocarbon group having a cyclic structure, which is represented as R in formula (I), include such as a cyclooctyl group, a cyclodecyl group, a cyclododecyl group, a cyclooctenyl group, a cyclodecenyl group, a cyclododecenyl group, a 2-(cyclohexyl)ethyl group, a 3-(cyclohexyl)propyl group, a 2-(cyclohexenyl)ethyl group, and a 3-(cyclohexenyl)propyl group.

In formula (I), n is an average added mole number of an ethyleneoxy group ($CH_2$—O—$CH_2$), and from the viewpoint of improving foamability or sense of use (for example, rinse-off property or slimy feeling) when used as a body cleansing agent, it is preferably 0.1 to 20, and more preferably 0.2 to 10.

n is even more preferably 1.0 to 6.0, even more preferably 2.0 to 5.5, and even more preferably 2.5 to 5.0.

When used as a body cleansing agent, from the viewpoint of improving foamability or sense of use (for example, rinse-off property or slimy feeling), $R^1$ and $R^2$ in formula (III) are each independently a linear alkyl group having 1 to 20 carbon atoms, preferably 1 to 18 carbon atoms, more preferably 1 to 16 carbon atoms, even more preferably 1 to 14 carbon atoms, and even more preferably 1 to 12 carbon atoms. A total number of carbons of $R^1$ and $R^2$ is, from the viewpoint of improving foamability or sense of use (for example, rinse-off property or slimy feeling) when used as a body cleansing agent, 3 to 21, preferably 7 to 17, more preferably 9 to 15, and even more preferably 11 to 13.

Specific examples of $R^1$ and $R^2$ in formula (III) include such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, and a nonadecyl group.

In formula (III), m is an average added mole number of an ethyleneoxy group (O—$CH_2$—$CH_2$), and from the viewpoint of improving foamability or sense of use (for example, rinse-off property or slimy feeling) when used as a body cleansing agent, it is a number 1.1 to 30, preferably 1.1 to 20, more preferably 1.2 to 10, even more preferably 2.0 to 6.0, even more preferably 3.0 to 5.5, and even more preferably 3.5 to 5.0.

The platinum catalyst used for the manufacturing method of the present invention is a catalyst containing platinum (Pt) as an active species from the viewpoint of catalytic activity. From the viewpoint of improving durability of the catalyst, a platinum catalyst supported on a support is preferable.

From the viewpoint of improving durability of the catalyst and improving handleability of the catalyst, the support is preferably an inorganic support. Examples thereof include activated carbon, alumina, silica gel, activated clay, and diatomaceous earth. Among them, activated carbon is preferable.

With regard to the platinum catalyst supported on a support, the amount of supported platinum is preferably 0.1 to 15% by mass, and more preferably 1.0 to 10% by mass in the solid matter of the catalyst from the viewpoint of suppressing the viscosity increase of the liquid phase during the reaction and improving the productivity of the polyoxyethylene alkyl ether acetic acid.

From the viewpoint of suppressing the production of an aldehyde and improving the productivity of the polyoxyethylene alkyl ether acetic acid, the platinum catalyst preferably contains a co-catalyst component.

Examples of the co-catalyst component include such as bismuth (Bi), lead (Pb), tin (Sn), gold (Au), ruthenium (Ru), and palladium (Pd). From the viewpoint of suppressing the production of an aldehyde and further improving the productivity, it is preferable to contain bismuth or lead. It is more preferable to contain bismuth.

When the co-catalyst component is contained, the amount of supported co-catalyst component in the platinum catalyst supported on a support is, from the viewpoint of suppressing the production of an aldehyde and improving the productivity, preferably 0.01 to 10% by mass, and more preferably 0.5 to 3.5% by mass in the solid matter of the catalyst.

The content ratio of the platinum to the co-catalyst component is, from the viewpoint of suppressing the production of an aldehyde and improving the productivity, preferably 0.05 to 1.0, and more preferably 0.1 to 0.6 in terms of co-catalyst component/platinum (in atomic ratio).

The platinum catalyst used for the manufacturing method of the present invention is manufactured by a known method in the field. For example, a method of impregnating a support component such as an activated carbon in an aqueous solution containing a pre-determined amount of platinum (and, if necessary, a co-catalyst component such as bismuth) and adsorbing the platinum (and the co-catalyst component) on the support component can be applied.

After the adsorption, a reduction treatment is performed using a reducing agent such as formalin, sodium borohydride, or hydrogen. The platinum catalyst is obtained by filtration and washing after reduction, and it can be used for the reaction even when it contains water or after being dried.

From the viewpoint of improving the productivity of a polyoxyethylene alkyl ether acetic acid, the platinum catalyst is preferably used such that the amount of platinum in the catalyst is 0.001 to 2.0 parts by mass, more preferably 0.01 to 1.5 parts by mass, and even more preferably 0.02 to 1.3 parts by mass relative to 100 parts by mass of the polyoxyethylene alkyl ether.

The dehydrogenating and oxidizing reaction of a polyoxyethylene alkyl ether is performed by feeding, in the presence of the platinum catalyst, oxygen to a liquid phase containing a polyoxyethylene alkyl ether and water.

The dehydrogenating and oxidizing reaction can be performed in a batch mode. For example, moreover, a circulating fixed bed type reaction apparatus with a fixed bed catalyst can be used, which has a structure as shown in FIG. 1 of JP-A 2008-94800.

At the time of the reaction, it is preferable not to add a base from the viewpoint of suppressing the generation of inorganic salts as side products.

Further, from the viewpoint of improving the productivity and suppressing the production of an aldehyde, the dehydrogenating and oxidizing reaction of a polyoxyethylene alkyl ether is preferably carried out under a condition of a pH of 7 or less, more preferably a pH of 1 to 7, even more preferably a pH of 2 to 7. The pH of the liquid phase at the time of starting the reaction is about 7, and as the polyoxyethylene alkyl ether acetic acid is manufactured in accordance with the progress of the reaction, the liquid phase gradually becomes acidic and the reaction is progressed in the state of a pH of 7 or less.

When no base is used at the time of the reaction for the manufacturing method of the present invention, generation of inorganic salts as side products, which is a problem in carboxymethylation or alkali neutralization oxidation corresponding to a technique of the related art, does not occur.

In the manufacturing method of the present invention, the mass ratio between the total mass of the polyoxyethylene alkyl ether and the polyoxyethylene alkyl ether acetic acid and the mass of water in the liquid phase (i.e., total mass of polyoxyethylene alkyl ether and polyoxyethylene alkyl ether acetic acid/mass of water) is 60/40 to 95/5 from the viewpoint of suppressing the viscosity increase of the liquid phase, suppressing the production of an aldehyde, and improving the productivity. Preferably, it is 65/35 to 93/7, more preferably 70/30 to 90/10, and even more preferably 75/25 to 85/15.

As described herein, content of water in the liquid phase indicates the total mass including water contained in other components such as a platinum catalyst as well as water added for the reaction.

By adjusting the mass ratio between the total mass of a polyoxyethylene alkyl ether and a polyoxyethylene alkyl ether acetic acid and the mass of water to be within the range described above, not only the significant viscosity increase according to the reaction can be suppressed but also the production of an aldehyde compound as a side product can be suppressed, and thus the polyoxyethylene alkyl ether acetic acid as an intended product can be obtained at a high yield. Although a detailed reason for obtaining such an effect remains unclear, it is assumed that a state having a high viscosity in which a water content is low and water forms a continuous phase changes into another phase having a low viscosity in which oil forms a continuous phase within the above disclosed range of the mass ratio of the total mass of a polyoxyethylene alkyl ether and a polyoxyethylene alkyl ether acetic acid to the mass of water.

In the manufacturing method of the present invention, the mass ratio between the polyoxyethylene alkyl ether and water in the liquid phase (i.e., mass of polyoxyethylene alkyl ether/mass of water) at the time of starting the reaction is, from the viewpoint of suppressing the viscosity increase of the liquid phase, suppressing the production of an aldehyde, and improving the productivity, preferably 60/40 to 95/5, more preferably 65/35 to 93/7, even more preferably 70/30 to 90/10, and even more preferably 75/25 to 85/15. As described herein, "at the time of starting the reaction" means the time point at which oxygen is fed into the liquid phase containing the polyoxyethylene alkyl ether and water in the presence of the platinum catalyst.

In the manufacturing method of the present invention, the total mass of a polyoxyethylene alkyl ether and a polyoxyethylene alkyl ether acetic acid in the liquid phase is, from the viewpoint of suppressing the viscosity increase of the liquid phase, suppressing the production of an aldehyde, and improving the productivity, preferably 60 to 95% by mass, more preferably 65 to 93% by mass, even more preferably 70 to 90% by mass, and even more preferably 75 to 85% by mass.

In the manufacturing method of the present invention, the mass of water in the liquid phase is, from the viewpoint of suppressing the viscosity increase of the liquid phase, suppressing the production of an aldehyde, and improving the productivity, preferably 5 to 40% by mass, more preferably 7 to 35% by mass, even more preferably 10 to 30% by mass, and even more preferably 15 to 25% by mass.

In the manufacturing method of the present invention, the total mass of the polyoxyethylene alkyl ether and water in the liquid phase at the time of starting the reaction is, from the viewpoint of suppressing the viscosity increase of the liquid phase, suppressing the production of an aldehyde, and improving the productivity, preferably 65% by mass or more, more preferably 72% by mass or more, even more preferably 80% by mass or more, even more preferably 90% by mass or more, and even more preferably 95% by mass or more.

In the manufacturing method of the present invention, as long as the content of water in the liquid phase is within the above range, an organic solvent may also be used in addition to water, if necessary. Examples of the organic solvent which may be used include glycol ethers such as dimethyl ether, diethyl ether, methyl ethyl ether, diethylene glycol dimethyl ether, triethylene glycol dimethyl ether, and propylene glycol ether, acetonitrile, and tert-butanol. From the viewpoint of suppressing the productivity from decreasing, the decreasing being due to removing an organic solvent, the content of the organic solvent in the liquid phase is preferably 50% by mass or less, more preferably 40% by mass or less, even more preferably 30% by mass or less, even more preferably 20% by mass or less, even more preferably 10% by mass or less, even more preferably 5% by mass or less, and even more preferably 0% by mass. Further, the total mass of water and the organic solvent in the liquid phase is, from the viewpoint of suppressing the productivity from decreasing, due to removing an organic solvent, preferably 5 to 50% by mass, more preferably 5 to 40% by mass, even more preferably 7 to 35% by mass even more preferably 10 to 30% by mass, and even more preferably 15 to 25% by mass.

Feeding oxygen into the liquid phase can be conducted by blowing oxygen gas or oxygen-containing mixture gas (e.g., air) into the liquid phase. Alternatively, it may also be performed by having a gas phase introduction of oxygen gas or an oxygen-containing mixture gas and carrying out the reaction under the atmosphere of those gases.

When oxygen-containing mixture gas is used, specific examples of the gas used in combination with oxygen are preferably so-called inert gas such as helium, argon, or nitrogen. The oxygen concentration in the gas is preferably 10% by volume or more, more preferably 20% by volume or more, even more preferably 50% by volume or more, even more preferably 70% by volume or more, and even more preferably 100% by volume.

The reaction temperature at the time of dehydrogenating and oxidizing a polyoxyethylene alkyl ether is, from the viewpoint of improving the reactivity and suppressing selectivity from decreasing, preferably 50 to 100° C., more preferably 50 to 80° C., and even more preferably 60 to 80° C. The reaction pressure may be any one of atmospheric pressure and an increased pressure.

According to the manufacturing method of the present invention, a polyoxyethylene alkyl ether acetic acid can be obtained at a high effective concentration only with a process of filtering the catalyst after completion of the reaction without requiring an operation of removing inorganic salts or a complicated operation for concentration, compared to a case in which carboxymethylation, alkali neutralization oxidation, or non-neutralization oxidation, being conventional, is applied.

When the compound represented by formula (I) is used as a polyoxyethylene alkyl ether for the manufacturing method of the present invention, it is possible to obtain a polyoxyethylene alkyl ether acetic acid which is represented by the following formula (II).

R—(CH$_2$—O—CH$_2$)$_n$—COOH    (II)

[in the formula, R and n have the same meanings as defined in formula (I)].

Further, regarding the manufacturing method of the present invention, when a compound represented by the above formula (III) is used as a polyoxyethylene alkyl ether, a polyoxyethylene alkyl ether acetic acid represented by the following formula (IV) can be obtained.

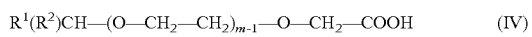

R$^1$(R$^2$)CH—(O—CH$_2$—CH$_2$)$_{m-1}$—O—CH$_2$—COOH    (IV)

[in the formula, R$^1$, R$^2$, and m have the same meanings as defined in formula (III)].

In the present invention, it is preferable that the polyoxyethylene alkyl ether is manufactured by the following step (1) and step (2):

(1) A step of adding ethylene oxide to an alcohol having a hydrocarbon group with 4 to 22 carbon atoms in the presence of an alkali catalyst to obtain a polyoxyethylene alkyl ether represented by formula (I).

(2) A step of decreasing the alcohol having a hydrocarbon group with 4 to 22 carbon atoms, which is included in the polyoxyethylene alkyl ether product mixture obtained from step (1), to 3.0% by mass or less.

Hereinbelow, step (1) and step (2) are explained in detail.
<Step (1)>

As for the alcohol having a hydrocarbon group with 4 to 22 carbon atoms which is used for Step (1), an alcohol having a hydrocarbon group with 6 to 16 carbon atoms is preferable, and an alcohol having a hydrocarbon group with 8 to 14 carbon atoms is more preferable from the viewpoint of exhibition of the performance of the polyoxyethylene alkyl ether acetic acid represented by formula (I) as a surfactant.

Specific examples of the alcohol having a hydrocarbon group with 4 to 22 carbon atoms include such as butanol, hexanol, octanol, decanol, dodecanol, tetradecanol, hexadecanol, octadecatnol, eiscosanol, and docosanol. From the viewpoint of exhibition of the performance of the ether acetic acid as a surfactant, hexanol, octanol, decanol, dodecanol, tetradecanol and hexadecanol are preferable.

As for the hydrocarbon group, a saturated or unsaturated aliphatic hydrocarbon group having a linear, branched, or cyclic structure is preferable. A linear or branched alkyl group or alkenyl group is more preferable. A linear or branched alkyl group is even more preferable. A linear alkyl group is even more preferable.

From the viewpoint of improving the reactivity and productivity, the reaction of Step (1) is performed in the presence of an alkali catalyst. Examples of the alkali catalyst include such as sodium hydroxide, potassium hydroxide, cesium hydroxide, magnesium hydroxide, and calcium hydroxide. From the viewpoint of the reactivity and easy availability, sodium hydroxide and potassium hydroxide are more preferable.

The addition reaction in Step (1) may be conducted in the same manner as Step (2) of Example 7, for example, and a polyoxyethylene alkyl ether represented by formula (I) can be obtained.

Meanwhile, in the manufacturing method of the present invention, a commercially available product such as EMULGEN 103, EMULGEN 106, or EMULGEN 108 manufactured by Kao Corporation may be used as a polyoxyethylene alkyl ether of formula (I) instead of performing Step (1).
<Step (2)>

In Step (2), from the viewpoint of improving the conversion rate and suppressing the generation of an aldehyde, the alcohol having a hydrocarbon group with 4 to 22 carbon atoms, which is included in the polyoxyethylene alkyl ether product mixture obtained from Step (1), is decreased preferably to 3.0% by mass or less, more preferably to 0.01 to 2.8% by mass, even more preferably to 0.05 to 2.5% by mass, even more preferably to 0.07 to 2.0% by mass, even more preferably to 0.09 to 1.5% by mass, and even more preferably to 0.1 to 1.0% by mass.

Although the reason remains unclear for increasing of the conversion rate by decreasing the alcohol having a hydrocarbon group with 4 to 22 carbon atoms, which is included in a polyoxyethylene alkyl ether product, to the aforementioned range, it is assumed that chemical species derived from an alcohol, containing no added alkylene oxide chain, inhibit the catalytic activity.

As for the method of decreasing the alcohol having a hydrocarbon group with 4 to 22 carbon atoms in Step (2), distillation, column separation, extraction, or the like can be mentioned. From the viewpoint of easy operability and removal efficiency, distillation and column separation are preferable. Distillation is more preferable.

As for the method of removing alcohol, it is preferable that a removal method based on distillation operation is applied.

The distillation operation is conducted by distillation of an alcohol with no added alkylene oxide, which has the lowest boiling point, by heating to 150° C. to 250° C. under a reduced pressure of several kPa to about 1 kPa. A polyoxyethylene alkyl ether is obtained as a distillation residue in which an alcohol not added with an alkylene oxide chain is reduced.

The dehydrogenating and oxidizing reaction of the polyoxyethylene alkyl ether obtained from Step (2) is performed by, as described above, feeding oxygen into a liquid phase containing the polyoxyethylene alkyl ether and water in the presence of the platinum catalyst.

As an exemplary embodiment of the present invention, the following manufacturing method or use is additionally described in the detailed description. However, the present invention is not limited to those embodiments.

<1> A method for manufacturing a polyoxyethylene alkyl ether acetic acid by feeding oxygen into a liquid phase containing a polyoxyethylene alkyl ether having a hydrocarbon group at the end (hereinbelow, it may be referred to as a polyoxyethylene alkyl ether) and water and dehydrogenating and oxidizing the polyoxyethylene alkyl ether in the presence of a platinum catalyst, in which the mass ratio of the total mass of the polyoxyethylene alkyl ether and the polyoxyethylene alkyl ether acetic acid to the mass of water in the liquid phase (i.e., total mass of polyoxyethylene alkyl ether and polyoxyethylene alkyl ether acetic acid/mass of water) is 60/40 to 95/5, preferably 65/35 to 93/7, more preferably 70/30 to 90/10, and even more preferably 75/25 to 85/15.

<2> The manufacturing method described in above <1>, in which the content of an organic solvent in the liquid phase is 50% by mass or less, preferably 40% by mass or less, more preferably 30% by mass or less, even more preferably 20% by mass or less, even more preferably 10% by mass or less, even more preferably 5% by mass or less, and even more preferably 0% by mass.

<3> The manufacturing method described in above <1>, in which the total content of water and the organic solvent in the liquid phase is 5 to 50% by mass, preferably 5 to 40% by mass, more preferably 7 to 35% by mass, even more preferably 10 to 30% by mass, and even more preferably 15 to 25% by mass.

<4> The method for manufacturing a polyoxyethylene alkyl ether acetic acid described in any one of above <1> to <3>, in which the mass ratio between the polyoxyethylene alkyl ether and water in the liquid phase at the time of starting the reaction (i.e., mass of polyoxyethylene alkyl ether/mass of water) is 60/40 to 95/5, preferably 65/35 to 93/7, more preferably 70/30 to 90/10, and even more preferably 75/25 to 85/15.

<5> The method for manufacturing a polyoxyethylene alkyl ether acetic acid described in any one of above <1> to <4>, in which the reaction is carried out under the condition of a pH of 7 or less, preferably a pH of 1 to 7, and more preferably a pH of 2 to 7.

<6> The method for manufacturing a polyoxyethylene alkyl ether acetic acid described in any one of above <1> to <5>, in which the polyoxyethylene alkyl ether is a compound represented by the following formula (I) and the polyoxyethylene alkyl ether acetic acid is a compound represented by the formula (II):

$$R-(CH_2-O-CH_2)_n-CH_2OH \quad (I)$$

$$R-(CH_2-O-CH_2)_n-COOH \quad (II)$$

in formula (I) and formula (II), R represents a hydrocarbon group having 3 to 21 carbon atoms, preferably 7 to 13 carbon atoms, and more preferably a hydrocarbon group having 9 to 13 carbon atoms and n represents an average added mole number of an ethyleneoxy group ($CH_2-O-CH_2$), which is a number of 0.1 to 30, preferably 0.1 to 20, more preferably 0.2 to 10, even more preferably 1.0 to 6.0, even more preferably 2.0 to 5.5, and even more preferably 2.5 to 5.0.

<7> The method for manufacturing a polyoxyethylene alkyl ether acetic acid described in any one of above <1> to <6>, in which the platinum catalyst is a platinum catalyst supported on a support.

<8> The method for manufacturing a polyoxyethylene alkyl ether acetic acid described in above <7>, in which the support is selected from activated carbon, alumina, silica gel, active white clay, and diatomaceous earth.

<9> The method for manufacturing a polyoxyethylene alkyl ether acetic acid described in above <7> or <8>, in which the support is activated carbon.

<10> The method for manufacturing a polyoxyethylene alkyl ether acetic acid described in any one of above <7> to <9>, in which the amount of supported platinum in the platinum catalyst supported on a support is 0.1 to 15% by mass, and preferably 1.0 to 10% by mass in the solid matter of the catalyst.

<11> The method for manufacturing a polyoxyethylene alkyl ether acetic acid described in any one of above <1> to <10>, in which the platinum catalyst contains a co-catalyst component.

<12> The method for manufacturing a polyoxyethylene alkyl ether acetic acid described in above <11>, in which the co-catalyst component is one or two or more kinds selected from bismuth, lead, tin, gold, ruthenium, and palladium.

<13> The method for manufacturing a polyoxyethylene alkyl ether acetic acid described in above <11> or <12>, in which the co-catalyst component is bismuth.

<14> The method for manufacturing a polyoxyethylene alkyl ether acetic acid described in any one of above <11> to <13>, in which the content ratio of the platinum and the co-catalyst component is, 0.05 to 1.0, and preferably 0.1 to 0.6 in terms of co-catalyst component/platinum (in atomic ratio).

<15> The method for manufacturing a polyoxyethylene alkyl ether acetic acid described in any one of above <1> to <14>, in which the platinum catalyst is used in such an amount that the amount of platinum in the catalyst is 0.001 to 2.0 parts by mass, preferably 0.01 to 1.5 parts by mass, and more preferably 0.02 to 1.3 parts by mass relative to 100 parts by mass of the polyoxyethylene alkyl ether.

<16> The method for manufacturing a polyoxyethylene alkyl ether acetic acid described in any one of above <1> to <15>, in which the reaction temperature is 50 to 100° C., preferably 50 to 80° C., and more preferably 60 to 80° C.

<17> The method for manufacturing a polyoxyethylene alkyl ether acetic acid described in any one of above <1> to <16>, in which the total mass of a polyoxyethylene alkyl ether and a polyoxyethylene alkyl ether acetic acid in the liquid phase is 60 to 95% by mass, preferably 65 to 93% by mass, more preferably 70 to 90% by mass, and even more preferably 75 to 85% by mass.

<18> The method for manufacturing a polyoxyethylene alkyl ether acetic acid described in any one of above <1> to <17>, in which the mass of water in the liquid phase is 5 to 40% by mass, preferably 7 to 35% by mass, more preferably 10 to 30% by mass, and even more preferably 15 to 25% by mass.

<19> The method for manufacturing a polyoxyethylene alkyl ether acetic acid described in any one of above <1> to <18>, in which the total mass of a polyoxyethylene alkyl ether and water in the liquid phase at the time of starting the reaction is 65% by mass or more, preferably 72% by mass or more, more preferably 80% by mass or more, even more preferably 90% by mass or more, and even more preferably 95% by mass or more.

<20> The method for manufacturing a polyoxyethylene alkyl ether acetic acid described in any one of above <1> to <19>, in which the polyoxyethylene alkyl ether is manufactured by the following Steps:

Step (1): a step of adding ethylene oxide to an alcohol having a hydrocarbon group with 4 to 22 carbon atoms, preferably 6 to 16 carbon atoms, and more preferably 8 to 14 carbon atoms in the presence of an alkali catalyst to obtain a polyoxyethylene alkyl ether represented by formula (I), and Step (2): a step of decreasing the alcohol having a hydrocarbon group with 4 to 22 carbon atoms, preferably 6 to 16 carbon atoms, and more preferably 8 to 14 carbon atoms, which is included in the polyoxyethylene alkyl ether product mixture obtained from Step (1), to 3.0% by mass or less, preferably to 0.01 to 2.8% by mass, more preferably to 0.05 to 2.5% by mass, even more preferably to 0.07 to 2.0% by mass, even more preferably to 0.09 to 1.5% by mass, and even more preferably to 0.1 to 1.0% by mass.

<21> The method for manufacturing a polyoxyethylene alkyl ether acetic acid described in above <20>, in which the alkali catalyst to be used in Step (1) is sodium hydroxide or potassium hydroxide.

<22> The method for manufacturing a polyoxyethylene alkyl ether acetic acid described in above <20> or <21>, in which the alcohol having a hydrocarbon group with 4 to 22 carbon atoms, preferably 6 to 16 carbon atoms, and more preferably 8 to 14 carbon atoms is decreased to 3.0% by mass or less, preferably to 0.01 to 2.8% by mass, more preferably to 0.05 to 2.5% by mass, even more preferably to 0.07 to 2.0% by mass, even more preferably to 0.09 to 1.5% by mass, and even more preferably to 0.1 to 1.0% by mass by distillation under reduced pressure, in Step (2).

<23> The method for manufacturing a polyoxyethylene alkyl ether acetic acid described in any one of above <1> to <22>, in which the polyoxyethylene alkyl ether is a compound represented by the following formula (I) or (III) and the polyoxyethylene alkyl ether acetic acid is a compound represented by the formula (II) or (IV):

$$R-(CH_2-O-CH_2)_n-CH_2OH \quad (I)$$

$$R-(CH_2-O-CH_2)_n-COOH \quad (II)$$

in formula (I) and formula (II), R represents a hydrocarbon group having 3 to 21 carbon atoms, preferably 7 to 13 carbon atoms, and even more preferably a hydrocarbon group having 9 to 13 carbon atoms and n represents an average added mole number of an ethyleneoxy group ($CH_2-O-CH_2$), which is a number of 0.1 to 30, preferably 0.1 to 20, more preferably 0.2 to 10, even more preferably 1.0 to 6.0, even more preferably 2.0 to 5.5, and even more preferably 2.5 to 5.0;

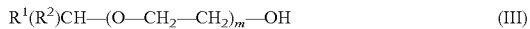

$$R^1(R^2)CH-(O-CH_2-CH_2)_m-OH \quad (III)$$

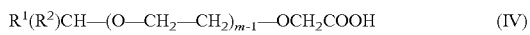

$$R^1(R^2)CH-(O-CH_2-CH_2)_{m-1}-OCH_2COOH \quad (IV)$$

in formula (III) and formula (IV), $R^1$ and $R^2$ each independently represent a linear alkyl group having 1 to 20 carbon atoms, preferably 1 to 18 carbon atoms, more preferably 1 to 16 carbon atoms, even more preferably 1 to 14 carbon atoms, and even more preferably 1 to 12 carbon atoms, total number of carbon atoms in $R^1$ and $R^2$ is from 3 to 21, preferably 7 to 17, more preferably 9 to 15, and even more preferably 11 to 13, and m represents an average added mole number of an ethyleneoxy group ($O-CH_2-CH_2$), which is a number of 1.1 to 30, preferably 1.1 to 20, more preferably 1.2 to 10, even more preferably 2.0 to 6.0, even more preferably 3.0 to 5.5, and even more preferably 3.5 to 5.0.

<24> The method for manufacturing a polyoxyethylene alkyl ether acetic acid described in above <23>, in which the polyoxyethylene alkyl ether is a compound represented by the following formula (III) and the polyoxyethylene alkyl ether acetic acid is a compound represented by the formula (IV):

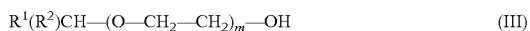

$$R^1(R^2)CH-(O-CH_2-CH_2)_m-OH \quad (III)$$

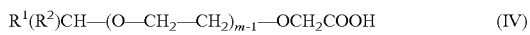

$$R^1(R^2)CH-(O-CH_2-CH_2)_{m-1}-OCH_2COOH \quad (IV)$$

in formula (III) and formula (IV), $R^1$ and $R^2$ each independently represent a linear alkyl group having 1 to 20 carbon atoms, preferably 1 to 18 carbon atoms, more preferably 1 to 16 carbon atoms, even more preferably 1 to 14 carbon atoms, and even more preferably 1 to 12 carbon atoms, total number of carbon atoms in $R^1$ and $R^2$ is from 3 to 21, preferably 7 to 17, more preferably 9 to 15, and even more preferably 11 to 13, and m represents an average added mole number of an ethyleneoxy group ($O-CH_2-CH_2$), which is a number of 1.1 to 30, preferably 1.1 to 20, more preferably 1.2 to 10, even more preferably 2.0 to 6.0, even more preferably 3.0 to 5.5, and even more preferably 3.5 to 5.0.

EXAMPLES

The following Examples are described as an embodiment of the present invention. Examples are described as an exemplification of the present invention and they are not given to limit the present invention.

<Measurement of Content and Conversion Rate of Polyoxyethylene Lauryl Ether Acetic Acid, Polyoxyethylene Lauryl Ether Aldehyde>

The contents of a polyoxyethylene lauryl ether acetic acid and a polyoxyethylene lauryl ether aldehyde in the reaction mixture which has been manufactured by the reaction were measured by conducting methyl esterification and determined with gas chromatography (GC) under the following condition, expressed as GC area % of the mole number of added EO up to 10 moles.

The conversion rate was calculated based on the GC analysis values of the polyoxyethylene lauryl ether which remains in the reaction mixture and the manufactured polyoxyethylene lauryl ether acetic acid.

<Quantification of Lauryl Alcohol in Polyoxyethylene Lauryl Ether>

An ethanol solution of lauryl alcohol at a normal concentration was prepared, and after GC measurement, a calibration curve was established based on the area obtained therefrom. Based on the calibration curve, the content of lauryl alcohol in a polyoxyethylene lauryl ether was obtained by an absolute calibration curve method.

(Conditions for GC)

GC apparatus; 6850 Series II manufactured by Agilent Technologies

Column; HP-ULTRA1 (25 m) manufactured by Agilent Technologies

Detector; FID

Carrier; Helium gas, 1 mL/min

Temperature increase; temperature is increased from 100° C. to 300° C. at 5° C./min, and thereafter maintained at 300° C. for 45 min.

<pH Measurement>

Using a pH controller, FD-02 Series B manufactured by Fine, a pH electrode was inserted into the reaction mixture, and by carrying out temperature correction with a temperature correction electrode, pH was measured.

Example 1

To a glass round-bottomed flask (internal volume of 0.5 L) equipped with a gas inlet, a gas outlet, a thermometer, a pH electrode and a stirrer including a Teflon (registered trademark) crescent stirring blade (blade area of 12.8 cm$^2$), 265 g of polyoxyethylene lauryl ether (i.e., a compound of formula (I) in which R—CH$_2$=lauryl group and n=4.6), 50 g of water, and 28 g of water containing platinum-bismuth catalyst supported on activated carbon (manufactured by Evonik Degussa, 5% by mass of platinum-1% by mass of bismuth in the catalyst solid matter, and 53% by mass of water in the apparent catalyst) were added, respectively. The pH of the liquid phase at 70° C. was 6.0 and the content of water in the liquid phase was 20% by mass.

After nitrogen purging at atmospheric pressure, temperature of the liquid phase was increased to 70° C. and stirring was carried out for 15 minutes under a nitrogen atmosphere.

After that, the introduction of nitrogen gas was terminated and oxygen gas was introduced at a rate of 90 mL/min and performed a gas phase introduction. The liquid phase was reacted for 7 hours under stirring at 400 rpm. During that period, the reaction system maintained at a low viscosity, and no increase in viscosity was observed. Further, the pH of the liquid phase was 3.0 after the reaction for 7 hours.

After the reaction for 7 hours, nitrogen-purging was performed and the reaction was terminated. The catalyst was separated by filtration from the reaction solution and the obtained reaction mixture was subjected to a gas chromatography analysis. As a result, it was found that the conversion rate of the polyoxyethylene lauryl ether was 70% and the content of the intended polyoxyethylene lauryl ether acetic acid was 64%. In addition, the production amount of the aldehyde was 1.9%. The reaction conditions and reaction results are shown in Table 1.

Example 2

The reaction was performed in the same manner as Example 1 except that 232 g of polyoxyethylene lauryl ether (i.e., a compound of formula (I) in which R—CH$_2$=lauryl group and n=2.9), 82 g of water, and 28 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added. The pH of the liquid phase at the time of starting the reaction was 5.8 and the content of water in the liquid phase was 30% by mass. The reaction system maintained at a low viscosity, and no increase in viscosity was observed.

After the reaction for 7 hours, the pH of the liquid phase was 2.9. It was found that the conversion rate of the polyoxyethylene lauryl ether is 64% and the content of the intended polyoxyethylene lauryl ether acetic acid is 55%. In addition, the production amount of the aldehyde was 3.7%. The reaction conditions and reaction results are shown in Table 1.

Example 3

The reaction was performed in the same manner as Example 1 except that 296 g of polyoxyethylene lauryl ether (i.e., a compound of formula (I) in which R—CH$_2$=lauryl group and n=4.6), 12 g of water, and 36 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added. The pH of the liquid phase at the time of starting the reaction was 6.1 and the content of water in the liquid phase was 10% by mass. The reaction system maintained at a low viscosity, and no increase in viscosity was observed.

After the reaction for 7 hours, the pH of the liquid phase was 3.2. It was found that the conversion rate of the polyoxyethylene lauryl ether is 57% and the content of the intended polyoxyethylene lauryl ether acetic acid is 49%. In addition, the production amount of the aldehyde was 3.4%. The reaction conditions and reaction results are shown in Table 1.

Example 4

The reaction was performed in the same manner as Example 1 except that 296 g of polyoxyethylene lauryl ether (i.e., a compound of formula (I) in which R—CH$_2$=lauryl group and n=4.6), 34 g of water, and 36 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added. The pH of the liquid phase at the time of starting the reaction was 6.1 and the content of water in the liquid phase was 16% by mass. The reaction system maintained at a low viscosity, and no increase in viscosity was observed.

After the reaction for 7 hours, the pH of the liquid phase was 3.0. It was found that the conversion rate of the polyoxyethylene lauryl ether is 66% and the content of the intended polyoxyethylene lauryl ether acetic acid is 59%. In addition, the production amount of the aldehyde was 2.8%. The reaction conditions and reaction results are shown in Table 1.

Example 5

The reaction was performed in the same manner as Example 1 except that 290 g of polyoxyethylene lauryl ether (i.e., a compound of formula (I) in which R—CH$_2$=mixture of lauryl group and myristyl group (75/25 (w/w)), and n=2.0), 15 g of water, and 36 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added. The pH of the liquid phase at the time of starting the reaction was 7.0 and the content of water in the liquid phase was 11% by mass. The reaction system maintained at a low viscosity, and no increase in viscosity was observed.

After the reaction for 7 hours, the pH of the liquid phase was 3.5. It was found that the conversion rate of the polyoxyethylene lauryl ether is 49% and the content of the intended polyoxyethylene lauryl ether acetic acid is 38%. In addition, the production amount of the aldehyde was 6.9%. The reaction conditions and reaction results are shown in Table 1.

Comparative Example 1

The reaction was performed in the same manner as Example 1 except that 70 g of polyoxyethylene lauryl ether (average added mole number of 4.6), 275 g of water, and 8.6 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added, respectively. The content of water in the liquid phase was 80% by mass. The reaction system had an increased viscosity.

After the reaction for 7 hours, the catalyst was separated by filtration from the reaction solution and the obtained reaction mixture was subjected to a gas chromatography analysis. As a result, it was found that the conversion rate of the polyoxyethylene lauryl ether is 8% and the content of the intended polyoxyethylene lauryl ether acetic acid is 6%. In addition, the production amount of the aldehyde was 1.4%. The reaction conditions and reaction results are shown in Table 1.

Comparative Example 2

The reaction was performed in the same manner as Example 1 except that 170 g of polyoxyethylene lauryl ether (average added mole number of 4.6), 157 g of water, and 21 g of water containing platinum-bismuth catalyst supported on activated carbon (manufactured by Evonik Degussa, 5% by mass of platinum-1% by mass of bismuth in the catalyst solid matter, and 59% by mass of water in the apparent catalyst) are added, respectively. The content of water in the liquid phase was 50% by mass. The reaction system showed an increased viscosity.

After the reaction for 7 hours, the catalyst was separated by filtration from the reaction solution and the obtained reaction mixture was subjected to a gas chromatography analysis. As a result, it was found that the conversion rate of the polyoxyethylene lauryl ether is 4% and the content of the intended polyoxyethylene lauryl ether acetic acid is 5%. In addition, the production amount of the aldehyde was 0.8%. The reaction conditions and reaction results are shown in Table 1.

Comparative Example 3

The reaction was performed in the same manner as Example 1 except that 339 g of polyoxyethylene lauryl ether (average added mole number of 4.6) and 24 g of a water-containing platinum-bismuth catalyst supported on activated carbon (manufactured by Evonik Degussa, 5% by mass of platinum-1% by mass of bismuth in the catalyst solid matter, and 30% by mass of water in the apparent catalyst) are added, respectively. The content of water in the liquid phase was 2% by mass. The reaction system maintained at a low viscosity, and no increase in viscosity was observed.

After the reaction, the catalyst was separated by filtration from the reaction solution and the obtained reaction mixture was subjected to a gas chromatography analysis. As a result, it was found that the conversion rate of the polyoxyethylene lauryl ether is 36% and the content of the intended polyoxyethylene lauryl ether acetic acid is 28%. In addition, the production amount of the aldehyde was 5.3%. The reaction conditions and reaction results are shown in Table 1.

TABLE 1

| | | Plutinum catalyst (supported amount relative to activated carbon) | feeding amount of liquid phase (g) | | | | (Aikyl ether + alkyl ether acetic acid)/water (mass ratio) | Content of water in liquid phase (mass %) | pH in liquid phase | | Conversion rate*2 (%) | Content of ether acetic acid*3 (GC area %) | Production content of aldehyde*4 (GC area %) |
|---|---|---|---|---|---|---|---|---|---|---|---|---|---|
| | | | AE1 | AE2 | AE3 | water*1 | | | At starting | After 7 hours | | | |
| Example | 1 | 5% Pt—1% Bi | 265 | — | — | 65 | 80/20 | 20 | 6.0 | 3.0 | 70 | 64 | 1.9 |
| | 2 | 5% Pt—1% Bi | — | 232 | — | 99 | 70/30 | 30 | 5.8 | 2.9 | 64 | 55 | 3.7 |
| | 3 | 5% Pt—1% Bi | 296 | — | — | 33 | 90/10 | 10 | 6.1 | 3.2 | 57 | 49 | 3.4 |
| | 4 | 5% Pt—1% Bi | 296 | — | — | 55 | 84/16 | 16 | 6.1 | 3.0 | 66 | 59 | 2.8 |
| | 5 | 5% Pt—1% Bi | — | — | 290 | 36 | 89/11 | 11 | 7.0 | 3.5 | 49 | 38 | 6.9 |
| Comparative example | 1 | 5% Pt—1% Bi | 70 | — | — | 280 | 20/80 | 80 | — | — | 8 | 6 | 1.4 |
| | 2 | 5% Pt—1% Bi | 170 | — | — | 169 | 50/50 | 50 | — | — | 5 | 4 | 0.8 |
| | 3 | 5% Pt—1% Bi | 339 | — | — | 7 | 98/2 | 2 | — | — | 36 | 28 | 5.3 |

AE1 starting material polyoxyethylene lauryl ether(alkyl: C12, added EO mole number of 4.6, EMULGEN 106)
AE2 starting material polyoxyethylene lauryl ether(alkyl: C12, added EO mole number of 2.9, EMULGEN 103)
AE3 starting material polyoxyethylene alkyl ether(alkyl: C12/C14 = 75/25(w/w), added EO mole number of 2.0, EMULGEN 102KG)
*1Total amount of water including the amount contained in the plutinum catalyst
*2Conversion rate of polyoxyethylene lauryl ether (after 7 hours)
*3Polyoxyethylene lauryl ether acetic acid (after 7 hours)
*4Polyoxyethylene lauryl ether aldehyde(after 7 hours)

Example 6

Step (1) and Step (2)

Instead of performing Step (1), as the polyoxyethylene alkyl ether represented by formula (I), EMULGEN 106 (catalyst for ethylene oxide addition: potassium hydroxide, addition product of 4.6 moles of lauryl alcohol/ethylene oxide, and from a quantitative GC analysis, lauryl alcohol is 5.7% by mass) manufactured by Kao Corporation was used.

Using the polyoxyethylene alkyl ether as a starting material, a distillation operation was performed under reduced pressure and the residual lauryl alcohol was removed by distillation. From the quantitative GC analysis of the distillation bottom, it was found that lauryl alcohol was 0.4% by mass.

Step (3)

To a glass round-bottomed flask (internal volume of 0.5 L) equipped with a gas inlet, a gas outlet, a thermometer, a pH electrode and a stirrer including a Teflon (registered trademark) crescent stirring blade (blade area of 12.8 cm$^2$), 265 g of the above polyoxyethylene lauryl ether (residual lauryl alcohol: 0.4% by mass), 50 g of water, and 32 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) were each added. The content of water in the liquid phase was 20% by mass.

After nitrogen-purging at atmospheric pressure, temperature of the liquid phase was increased to 70° C. and stirring was carried out for 15 minutes under a nitrogen atmosphere. After that, the introduction of the nitrogen gas was terminated and oxygen gas was introduced at a rate of 90 mL/min and performed a gas phase introduction. The liquid phase was reacted for 7 hours under stirring at 400 rpm. After the reaction for 7 hours, nitrogen-purging was performed and the reaction was terminated.

The catalyst was separated by filtration from the reaction solution and the obtained reaction mixture was subjected to a gas chromatography analysis. As a result, it was found that the conversion rate of the polyoxyethylene lauryl ether was 91% and the content of the polyoxyethylene lauryl ether acetic acid as an intended product was 87%.

Example 7

Step (1)

To a 6 L autoclave, 2770 g of lauryl alcohol and 5.12 g of potassium hydroxide were added. After nitrogen-purging, a dehydration operation was performed under reduced pressure at 110° C. After that, the temperature was increased to 155° C. and 1930 g of ethylene oxide were slowly injected under pressure After completing the injection under pressure, the reaction was performed for 1 hour, and then cooled.

Based on the hydroxyl value of the product obtained, an added mole number of ethylene oxide was 3.6 moles, and from the quantitative GC analysis, lauryl alcohol was 8.7% by mass.

Step (2)

Distillation operation under reduced pressure was performed using, as a starting material, the polyoxyethylene alkyl ether obtained from Step (1) and the residual lauryl alcohol was removed by distillation. From the GC analysis of the distillation bottom, lauryl alcohol was found to be 0.2% by mass.

Step (3)

The dehydrogenation and oxidization was performed in the same manner as Example 5 except that the polyoxyethylene alkyl ether (residual lauryl alcohol: 0.2% by mass) obtained from Step (2) was used as a starting material.

As a result, the conversion rate of the polyoxyethylene lauryl ether after 9 hours was 90% and the content of the polyoxyethylene lauryl ether acetic acid as an intended product was 86%.

Example 8

Step (1) and Step (2)

In the same manner as Example 6, a polyoxyethylene alkyl ether in which the content of lauryl alcohol was 1.3% by mass was prepared using EMULGEN 106 as a starting material.

Step (3)

Further, the dehydrogenating and oxidizing reaction was performed for 7 hours in the same manner as Example 6. As a result, the conversion rate of the polyoxyethylene lauryl ether was 85% and the content of the polyoxyethylene lauryl ether acetic acid as an intended product was 83%.

Example 9

Step (1) and Step (2)

In the same manner as Example 6, a polyoxyethylene alkyl ether in which the content of lauryl alcohol was 2.3% by weight was prepared using EMULGEN 106 as a starting material.

Step (3)

Further, the dehydrogenating and oxidizing reaction was performed for 7 hours in the same manner as Example 6. As a result, the conversion rate of the polyoxyethylene lauryl ether was 80% and the content of the polyoxyethylene lauryl ether acetic acid as an intended product was 77%.

Example 10

To a glass round-bottomed flask (internal volume of 0.5 L) equipped with a stirrer including a gas inlet, a gas outlet, a thermometer, a pH electrode, and a Teflon (registered trademark) crescent stirring blade (blade area of 12.8 cm$^2$), 265 g of polyoxyethylene lauryl ether (i.e., a compound of formula (I) in which n=4.6: EMULGEN 106 manufactured by Kao Corporation; from a quantitative GC analysis, lauryl alcohol is 5.7% by mass), 50 g of water, and 32 g of a water-containing platinum-bismuth catalyst supported on activated carbon (manufactured by Evonik Degussa, 5% by mass of platinum-1% by mass of bismuth in the catalyst solid matter, and 59% by mass of water in the apparent catalyst) were added, respectively. The content of water in the liquid phase was 20% by mass.

After nitrogen-purging at atmospheric pressure, temperature of the liquid phase was increased to 70° C. and stirring was carried out for 15 minutes under a nitrogen atmosphere. After that, the introduction of the nitrogen gas was terminated and oxygen gas was introduced at a rate of 90 mL/min and performed a gas phase introduction. The liquid phase was reacted for 7 hours under stirring at 400 rpm. After the reaction for 7 hours, nitrogen-purging was performed and the reaction was terminated.

The catalyst was separated by filtration from the reaction solution and the obtained reaction mixture was subjected to a gas chromatography analysis. As a result, it was found that the conversion rate of the polyoxyethylene lauryl ether was 72% and the content of the polyoxyethylene lauryl ether acetic acid as an intended product was 66%.

Example 11

The dehydrogenation and oxidization was performed in the same manner as Example 7 except that Step (2) of removing lauryl alcohol by distillation was not performed.

As a result, the conversion rate of the polyoxyethylene lauryl ether 9 hours after the reaction was 68% and the content of the polyoxyethylene lauryl ether acetic acid as an intended product was 59%.

The reaction conditions and reaction results of Examples 6 to 11 are shown in Table 2.

TABLE 2

| | step (1) | | step (2) | Process (3) | | | | | | |
|---|---|---|---|---|---|---|---|---|---|---|
| | Polyoxyethylene lauryl ether as a starting material | | Content of lauryl | Platinum catalyst (supported | Polyoxyethylene | | | | | Content of |
| | Added mole number of EO | Content of lauryl ether alcohol (% by mass) | alcohol after distillation operation (% by mass) | amount relative to activated carbon) | lauryl ether/water (mass ratio) at the time of starting the reaction | Reaction time (hr) | pH in liquid phase | | Conversion rate (%) | ether acetic acid (GC area %)) |
| | | | | | | | At starting | At ending | | |
| Example 6 | 4.6 | 5.7 | 0.4 | 5% Pt—1% Bi | 80/20 | 7 | 7.0 | 2.8 | 91 | 87 |
| Example 7 | 3.6 | 8.7 | 0.2 | 5% Pt—1% Bi | 80/20 | 9 | 6.9 | 3.2 | 90 | 86 |
| Example 8 | 4.6 | 5.7 | 1.3 | 5% Pt—1% Bi | 80/20 | 7 | 7.0 | 3.1 | 85 | 83 |
| Example 9 | 4.6 | 5.7 | 2.3 | 5% Pt—1% Bi | 80/20 | 7 | 7.0 | 3.0 | 80 | 77 |
| Example 10 | 4.6 | 5.7 | — | 5% Pt—1% Bi | 80/20 | 7 | 6.8 | 3.4 | 72 | 66 |
| Example 11 | 3.6 | 8.7 | — | 5% Pt—1% Bi | 80/20 | 9 | 7.0 | 2.9 | 68 | 59 |

Example 12

To a glass round-bottomed flask (internal volume of 0.5 L) equipped with a gas inlet, a gas outlet, a thermometer, a pH electrode and a stirrer including a Teflon (registered trademark) crescent stirring blade (blade area of 12.8 cm$^2$), 265 g of a polyoxyethylene alkyl ether (i.e., a compound of formula (III) in which total carbon number of $R^1$ and $R^2$ is 10 to 14, and m=5.0, product name: EMULGEN 705), 47 g of water, and 33 g of a water-containing platinum-bismuth catalyst supported on activated carbon (manufactured by Evonik Degussa, 5% by mass of platinum-1% by mass of bismuth in the catalyst solid matter, and 60% by mass of water in the apparent catalyst) were each added. The pH of the liquid phase at 70° C. was 6.6 and the content of water in the liquid phase was 20% by mass.

After nitrogen-purging at atmospheric pressure, temperature of the liquid phase was increased to 70° C. and stirring was carried out for 15 minutes under a nitrogen atmosphere.

After that, the introduction of the nitrogen gas was terminated and oxygen gas was introduced at a rate of 90 mL/min and performed a gas phase introduction. The liquid phase was reacted for 7 hours under stirring at 400 rpm. During that period, the reaction system maintained at a low viscosity, and no increase in viscosity was observed. Further, the pH of the liquid phase was 3.0 after the reaction for 7 hours.

After the reaction for 7 hours, nitrogen-purging was performed and the reaction was terminated. The catalyst was separated by filtration from the reaction solution and the obtained reaction mixture was subjected to acid number measurement. As a result, the acid number was found to be 58. Based on the acid number expected from the hydroxyl value (131) of the polyoxyethylene alkyl ether as a starting material, the content of the polyoxyethylene alkyl ether acetic acid was 58%.

The invention claimed is:

1. A method for manufacturing a polyoxyethylene alkyl ether acetic acid, comprising feeding oxygen into a liquid phase containing a polyoxyethylene alkyl ether having a hydrocarbon group at the end and water and dehydrogenating and oxidizing the polyoxyethylene alkyl ether in the presence of a platinum catalyst, wherein the platinum catalyst comprises bismuth as a co-catalyst component, and
wherein the mass ratio of the total mass of the polyoxyethylene alkyl ether and the polyoxyethylene alkyl ether acetic acid to the mass of water in the liquid phase, that is total mass of polyoxyethylene alkyl ether and polyoxyethylene alkyl ether acetic acid/mass of water, is 60/40 to 95/5 at the time of starting the reaction.

2. The manufacturing method according to claim 1, wherein the liquid phase contains an organic solvent in an amount of 50% by mass or less.

3. The manufacturing method according to claim 2, wherein the total amount of water and the organic solvent in the liquid phase is 50% by mass or less.

4. The method for manufacturing a polyoxyethylene alkyl ether acetic acid according to claim 1, wherein the reaction is carried out under a condition of a pH of 7 or less.

5. The method for manufacturing a polyoxyethylene alkyl ether acetic acid according to claim 1, wherein the polyoxyethylene alkyl ether is a compound represented by the following formula (I) and the polyoxyethylene alkyl ether acetic acid is a compound represented by the formula (II):

R—(CH$_2$—O—CH$_2$)$_n$—CH$_2$OH    (I)

R—(CH$_2$—O—CH$_2$)$_n$—COOH    (II)

in formula (I) and formula (II), R represents a hydrocarbon group having 3 to 21 carbon atoms and n represents an average added mole number of an ethyleneoxy group (CH$_2$—O—CH$_2$), which is a number of 0.1 to 30.

6. The method for manufacturing a polyoxyethylene alkyl ether acetic acid according to claim 1, wherein the reaction is carried out at a temperature of 50° C. to 100° C.

7. The method for manufacturing a polyoxyethylene alkyl ether acetic acid according to claim 1, wherein the polyoxyethylene alkyl ether is manufactured by the following steps:
  (1) a step of adding ethylene oxide to an alcohol having a hydrocarbon group with 4 to 22 carbon atoms in the presence of an alkali catalyst to obtain a polyoxyethylene alkyl ether represented by formula (I), and
  (2) a step of decreasing the alcohol having a hydrocarbon group with 4 to 22 carbon atoms, which is included in the polyoxyethylene alkyl ether product mixture obtained from step (1), to 3.0% by mass or less.

8. The method for manufacturing a polyoxyethylene alkyl ether acetic acid according to claim 7, wherein the alkali catalyst used in step (1) is sodium hydroxide or potassium hydroxide.

9. The method for manufacturing a polyoxyethylene alkyl ether acetic acid according to claim 7, wherein the alcohol having a hydrocarbon group with 4 to 22 carbon atoms is decreased to 3.0% by mass or less by distillation under a reduced pressure in step (2).

10. The method for manufacturing a polyoxyethylene alkyl ether acetic acid according to claim 1, wherein the mass ratio of the total mass of the polyoxyethylene alkyl ether and the polyoxyethylene alkyl ether acetic acid to the mass of water in the liquid phase (the total mass of polyoxyethylene alkyl ether and polyoxyethylene alkyl ether acetic acid/mass of water) is 70/30 to 90/10 at the time of starting the reaction.

11. The method for manufacturing a polyoxyethylene alkyl ether acetic acid according to claim 1, wherein the mass ratio of the total mass of the polyoxyethylene alkyl ether and the polyoxyethylene alkyl ether acetic acid to the mass of water in the liquid phase (the total mass of polyoxyethylene alkyl ether and polyoxyethylene alkyl ether acetic acid/mass of water) is 75/25 to 85/15 at the time of starting the reaction.

12. The method for manufacturing a polyoxyethylene alkyl ether acetic acid according to claim 1, wherein the content of an organic solvent in the liquid phase is 10% by mass or less.

13. The method for manufacturing a polyoxyethylene alkyl ether acetic acid according to claim 1, wherein the content of an organic solvent in the liquid phase is 0% by mass.

14. The method for manufacturing a polyoxyethylene alkyl ether acetic acid according to claim 2, wherein the total amount of water and the organic solvent in the liquid phase is 10 to 30% by mass.

15. The method for manufacturing a polyoxyethylene alkyl ether acetic acid according to claim 2, wherein the total amount of water and the organic solvent in the liquid phase is 15 to 25% by mass.

16. The method for manufacturing a polyoxyethylene alkyl ether acetic acid according to claim 1, wherein R in formula (I) and formula (II) represents a hydrocarbon group having 9 to 13 carbon atoms and n is a number of 2.5 to 5.0.

17. The method for manufacturing a polyoxyethylene alkyl ether acetic acid according to claim 1, wherein the atomic ratio of the platinum and a co-catalyst component is 0.1 to 0.6 in terms of co-catalyst component/platinum.

18. The method for manufacturing a polyoxyethylene alkyl ether acetic acid according to claim 7, wherein the step (2) is a step of decreasing the alcohol having a hydrocarbon group with 8 to 14 carbon atoms, which is included in the polyoxyethylene alkyl ether product mixture obtained from Step (1), to 0.1 to 1.0% by mass.

* * * * *